US012337048B2

(12) United States Patent
Gupta et al.

(10) Patent No.: US 12,337,048 B2
(45) Date of Patent: *Jun. 24, 2025

(54) ORAL CARE COMPOSITIONS COMPRISING TIN IONS

(71) Applicant: The Procter & Gamble Company, Cincinnati, OH (US)

(72) Inventors: Shikhar Gupta, Singapore (SG); Guannan Wang, Beijing (CN); Ross Strand, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 763 days.

This patent is subject to a terminal disclaimer.

(21) Appl. No.: 17/408,839

(22) Filed: Aug. 23, 2021

(65) Prior Publication Data

US 2022/0133606 A1 May 5, 2022
US 2024/0293296 A9 Sep. 5, 2024

Related U.S. Application Data

(63) Continuation of application No. 16/911,415, filed on Jun. 25, 2020, now Pat. No. 11,135,143.

(30) Foreign Application Priority Data

Jun. 28, 2019 (WO) ................ PCT/CN2019/093507

(51) Int. Cl.
*A61K 8/21* (2006.01)
*A61K 8/24* (2006.01)
*A61K 8/25* (2006.01)
*A61K 8/27* (2006.01)
*A61K 8/34* (2006.01)
*A61Q 11/00* (2006.01)

(52) U.S. Cl.
CPC ................. *A61K 8/21* (2013.01); *A61K 8/24* (2013.01); *A61K 8/25* (2013.01); *A61K 8/27* (2013.01); *A61K 8/345* (2013.01); *A61Q 11/00* (2013.01); *A61K 2800/48* (2013.01); *A61K 2800/52* (2013.01); *A61K 2800/88* (2013.01)

(58) Field of Classification Search
CPC ... A61K 8/21; A61K 8/24; A61K 8/25; A61K 8/27; A61K 8/345; A61K 2800/48; A61K 2800/52; A61K 2800/88; A61K 2800/49; A61K 2800/51; A61K 2800/92; A61K 8/19; A61K 8/60; A61Q 11/00
See application file for complete search history.

(56) References Cited

U.S. PATENT DOCUMENTS

| | | |
|---|---|---|
| 3,920,849 A | 11/1975 | Marmo |
| 3,962,417 A | 6/1976 | Howell |
| 4,159,347 A | 6/1979 | Vock et al. |
| 4,902,497 A | 2/1990 | Crisanti |
| 5,338,537 A | 8/1994 | White, Jr. et al. |
| 5,348,733 A | 9/1994 | Morishima |
| 9,011,825 B2 | 4/2015 | Midha et al. |
| 9,687,427 B2 | 6/2017 | Li et al. |
| 10,195,124 B2 | 2/2019 | Prencipe |
| 10,213,368 B2 | 2/2019 | Li et al. |
| 2003/0007937 A1* | 1/2003 | Lawlor ............... A61K 8/27 424/57 |
| 2008/0286214 A1 | 11/2008 | Brown |
| 2008/0311055 A1 | 12/2008 | Futterer |
| 2012/0276023 A1 | 11/2012 | Shimohirao |
| 2014/0037555 A1 | 2/2014 | Hoke |
| 2014/0227202 A1 | 8/2014 | Pilgaonkar |
| 2016/0324738 A1 | 11/2016 | Baig |
| 2017/0105911 A1 | 4/2017 | Budde |
| 2017/0157171 A1 | 6/2017 | Gerard |
| 2017/0333310 A1 | 11/2017 | Subramanyam |
| 2017/0348206 A1 | 12/2017 | Vemishetti et al. |
| 2018/0214356 A1 | 8/2018 | Hilke |
| 2020/0405593 A1 | 12/2020 | Baig et al. |
| 2020/0405594 A1 | 12/2020 | Baig et al. |
| 2020/0405595 A1 | 12/2020 | Gupta et al. |
| 2021/0378922 A1 | 12/2021 | Baig et al. |
| 2021/0393491 A1 | 12/2021 | Baig et al. |

FOREIGN PATENT DOCUMENTS

| | | |
|---|---|---|
| CN | 104069013 A | 10/2014 |
| CN | 105997743 A | 10/2016 |
| CN | 107072888 A | 8/2017 |
| CN | 107235634 A | 10/2017 |
| CN | 107530240 A | 1/2018 |
| CN | 108472213 A | 8/2018 |

(Continued)

OTHER PUBLICATIONS

All Office Actions; U.S. Appl. No. 18/498,468, filed on Oct. 31, 2023.
All Office Actions; U.S. Appl. No. 18/498,485, filed on Oct. 31, 2023.
Unpublished U.S. Appl. No. 18/498,468, filed on Oct. 31, 2023, Arif Ali Baig et al.
Unpublished U.S. Appl. No. 18/498,485, filed on Oct. 31, 2023, Arif Ali Baig et al.

(Continued)

*Primary Examiner* — Snigdha Maewall
(74) *Attorney, Agent, or Firm* — John G. Powell; Elizabeth A. Conklin

(57) ABSTRACT

An oral care composition with a tin, polyol with five or six carbon atoms, polyol with seven or more hydroxyl functional groups, and a pH of greater than 7. An oral care composition with a tin ion source, a fluoride ion source, a polyol with five or six carbon atoms, a non reducing sugar or sugar alcohol with seven or more hydroxyl functional groups, and a pH of greater than 7. Oral care compositions with a high tin ion availability.

20 Claims, 6 Drawing Sheets

(56) References Cited

FOREIGN PATENT DOCUMENTS

| | | |
|---|---|---|
| EP | 0514966 A2 | 11/1992 |
| EP | 0941671 A2 | 9/1999 |
| EP | 2057978 A1 | 5/2009 |
| GB | 2216005 A | 10/1989 |
| JP | S5651409 A | 5/1981 |
| JP | H05148125 A | 6/1993 |
| JP | H09503506 A | 4/1997 |
| JP | 2003128529 A | 5/2003 |
| JP | 2012219038 A | 11/2012 |
| JP | 2015083547 A | 4/2015 |
| JP | 2017052700 A | 3/2017 |
| JP | 2017519797 A | 7/2017 |
| WO | 9509602 A1 | 4/1995 |
| WO | 9712523 A1 | 4/1997 |
| WO | 0132135 A1 | 5/2001 |
| WO | 2015105438 A1 | 7/2015 |
| WO | 2016093279 A1 | 6/2016 |
| WO | 2016105438 A1 | 6/2016 |
| WO | 2016178652 A1 | 11/2016 |
| WO | 2020264570 A1 | 12/2020 |

OTHER PUBLICATIONS

All Office Actions, U.S. Appl. No. 16/911,412.
All Office Actions, U.S. Appl. No. 16/911,414.
All Office Actions, U.S. Appl. No. 16/911,415.
15572M PCT Search Report and Written Opinion for PCT/US2020/070178 dated Sep. 17, 2020.
15573M PCT Search Report and Written Opinion for PCT/US2020/070179 dated Oct. 6, 2020.
15574M PCT Search Report and Written Opinion for PCT/US2020/070186 dated Oct. 20, 2020.
PCT Search Report 15574F—PCT/CN2019/093507 dated Jun. 28, 2019.
All Office Actions; U.S. Appl. No. 17/408,782, filed on Aug. 23, 2021.
All Office Actions; U.S. Appl. No. 17/408,803, filed on Aug. 23, 2021.
Anonymous: "Crystal Whitening Toothpaste", Database GNPD [Online] Mintel; Database accession No. 7299787, dated Feb. 28, 2020, 4 pages.

* cited by examiner

ORAL CARE COMPOSITIONS COMPRISING TIN IONS

FIELD OF THE INVENTION

The present invention relates to compositions comprising tin, polyol with five or six carbon atoms, and polyol with seven or greater hydroxyl functional groups at a pH of greater than 7. The present invention also relates to oral care compositions comprising stannous fluoride, stabilizing polyol, and gum strengthening polyol at a pH of greater than 7.

BACKGROUND OF THE INVENTION

Sources of tin ions, such as stannous fluoride, are added to dentifrice compositions to deliver antimicrobial and anti-sensitivity benefits. However, tin ion sources can be difficult to incorporate into dentifrice compositions due to (i) the reactivity between tin ions and other dentifrice components, such as silica, and (ii) the formation of insoluble tin compounds at particular pH conditions. Thus, the incorporation of tin ions into dentifrice compositions is only possible by minimizing interactions between tin ions and key dentifrice components during storage to maximize tin ion availability for reactivity with oral cavity surfaces, such as enamel, dentine, gums, plaque, and bacteria.

The chemical instability in solution of tin ions can be mitigated by lowering the pH of the solution, providing anionic chelants, such as anions of organic acids, or providing polymeric chelants, such as polyphosphates or polycarboxylates. Some of these chelants can also prevent tin ion interactions with the surface of silica molecules by binding directly to the tin ions. However, strong chelant-tin ion interactions can also be detrimental to tin ion availability if the chelant-tin ion interactions are stronger than binding affinity between tin ions and intra oral surfaces, such tin ion delivery is a prerequisite for performance against diseases of the oral cavity such as plaque, gingivitis, malodor, caries, sensitivity, and dental erosion etc. Thus, even chelant selection must be balanced with the overall dentifrice formulation to maximize tin ion availability.

Due to the chemical instability of tin ions in aqueous-based dentifrice compositions, stannous fluoride is not typically used in aqueous compositions without the use of chelants, such as gluconate or citrate. Moreover, high pH aqueous dentifrice compositions are even less preferred due to the potential formation of $Sn(OH)_2$, which can precipitate out of the dentifrice composition at a pH of greater than 7. Anhydrous conditions can be used to formulate stable compositions with stannous fluoride. Polyols, such as glycerin, sorbitol, and xylitol can be added to anhydrous dentifrice compositions as a replacement carrier material in place of water. However, polyols can be expensive relative to other carrier materials in water-based dentifrice compositions. Accordingly, there is a need for a stable, water-based dentifrice composition that does not require chelants, which can be detrimental to the tin ion availability in the dentifrice composition.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Disclosed herein is an oral care composition comprising (a) from about 0.0025% to about 5%, by weight of the oral care composition, of a tin ion source; (b) from about 5% to about 50%, by weight of the oral care composition, of a stabilizing polyol having from five or six carbon atoms; (c) from about 0.0025% to about 20%, by weight of the oral care composition, of a gum strengthening polyolpolyol having seven or more hydroxyl functional groups, and (d) up to about 45%, by weight of the oral care composition, of water, wherein the oral care composition has a pH of greater than 7.

Disclosed herein is an oral care composition comprising (a) from about 0.0025% to about 5%, by weight of the oral care composition, of a tin ion source; (b) from about 5% to about 50%, by weight of the oral care composition, of a stabilizing polyol having from five or six carbon atoms; (c) from about 0.0025% to about 20%, by weight of the oral care composition, of a gum polyol having seven or more hydroxyl functional groups, and (d) from about 45% to about 75%, by weight of the oral care composition, of water, wherein the oral care composition has a pH of greater than 7.

Disclosed herein is an oral care composition comprising (a) from about 0.0025% to about 5%, by weight of the oral care composition, of a tin ion source, (b) from about 0.0025% to about 5%, by weight of the oral care composition, of a fluoride ion source, the fluoride ion source comprising sodium fluoride, sodium monofluorophosphate, amine fluoride, or combinations thereof, (c) from about 5% to about 50%, by weight of the oral care composition, of a stabilizing polyol having from five or six carbon atoms; (d) from about 0.0025% to about 20%, by weight of the oral care composition, of a gum strengthening polyol having seven or more hydroxyl functional groups, and (e) from about 10% to about 45%, by weight of the oral care composition, of water, wherein the oral care composition has a pH of greater than 7.

Disclosed herein is an oral care composition comprising (a) from about 0.0025% to about 5%, by weight of the oral care composition, of a tin ion source, (b) from about 5% to about 50%, by weight of the oral care composition, of a stabilizing polyol having five or six carbon atoms; (c) from about 0.0025% to about 20%, by weight of the oral care composition, of a gum strengthening polyol having seven or more hydroxyl functional groups, and (d) from about 75% to about 99%, by weight of the composition, of water, wherein the oral composition has a pH of greater than 7.

DETAILED DESCRIPTION OF THE INVENTION

Figure 1:
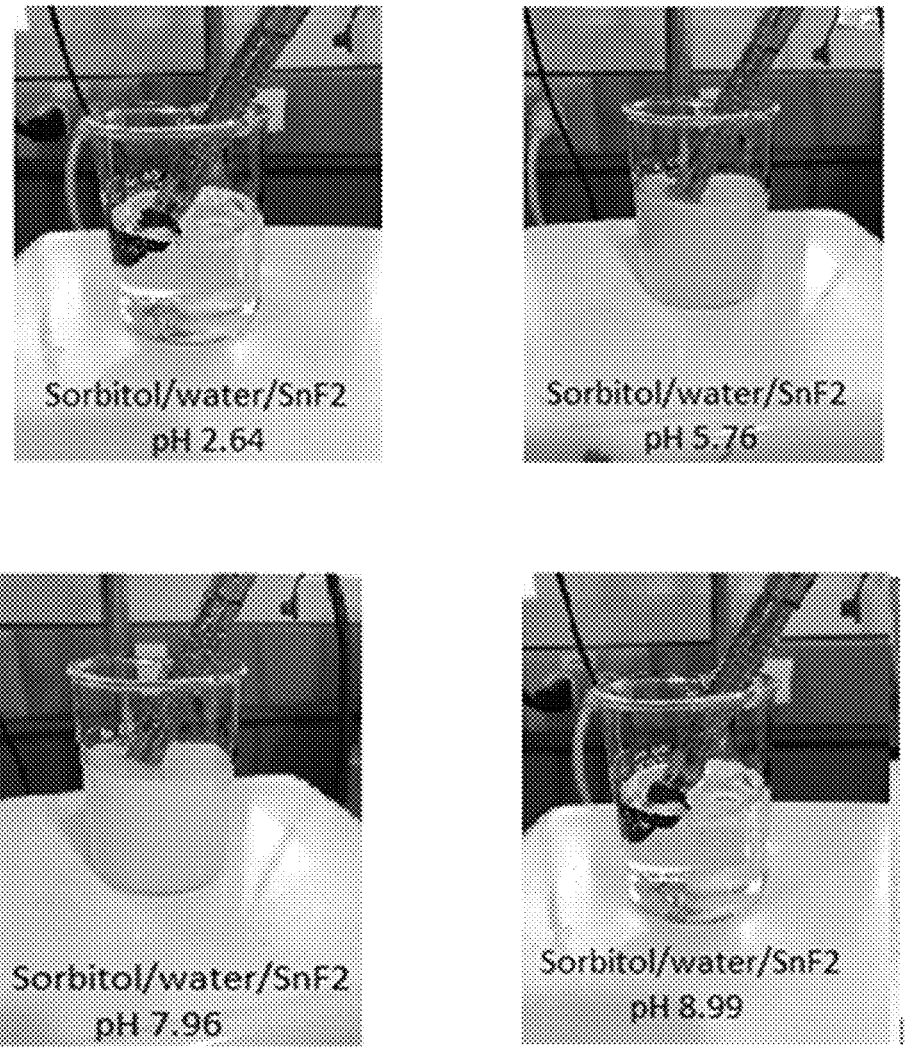
FIG. 1 is an illustration of the solubilization of tin ions at various pH conditions with sorbitol.

The present invention is directed to oral care compositions comprising a tin ion source, a polyol with five or six carbon atoms, and a polyol with seven or more carbon atoms at a pH of greater than 7 or from about 7.5 to about 10.

Tin ion sources are not typically used in aqueous dentifrice compositions at a pH of greater than 7 due to the formation of $Sn(OH)_2$, which can precipitate out of the dentifrice composition immediately upon mixing or while the dentifrice composition is stored prior to use by a consumer, thereby eliminating any benefit derived from free tin ions.

As such, aqueous dentifrice compositions comprising a tin ion source at a pH of greater than 7 are typically not expected to be compatible. Unexpectedly, and as described herein, stable dentifrice compositions comprising a tin ion source and a polyol with five or more atoms at a pH of greater than 7 have been found to be shelf stable with minimal or no formation of $Sn(OH)_2$. Without wishing to be bound by theory, it is believed that when dentifrice compositions comprising a tin ion source and a polyol with five or more carbon atoms are properly formulated, the polyol with five or more carbon atoms can weakly interact with the free tin ions to prevent the formation of insoluble $Sn(OH)_2$ at elevated pH conditions.

In regard to the highly specified cell-to-cell junctions and high renewal capabilities, gingival epithelium is considered a strong but passive barrier and is constantly exposed to environmental stimulation by (i) the rich and diverse tooth adherent microbiome and bacterial challenges and (ii) the continuous barrier damage arising from chewing and hygiene regimens.

The gingival epithelial cells are one of the first host cell types that are in constant contact with bacterial products. Loss of epithelial integrity, barrier and disruption has been associated with invasion of bacteria into underlying connective tissues, potentially increasing the inflammatory response and the subsequent tissue damage, characteristic of gingivitis and periodontal disease.

Unexpectedly, and as described herein, polyols with seven or more hydroxyl functional groups can additionally lead to an improvement in the barrier function of epithelial surfaces found in the oral cavity. While polyols with seven or more hydroxyl functional groups can (i) stabilize tin ions and/or (ii) improve the barrier function of epithelial surfaces found in the oral cavity, polyols with seven or more hydroxyl functional groups can be cost prohibitive when added to oral care compositions in the needed amounts. Thus, the present invention is also directed to oral care compositions with a tin ion source, a stabilizing polyol having five or six carbon atoms, and a gum polyol with seven or more hydroxyl functional groups.

While the specification concludes with claims particularly pointing out and distinctly claiming the invention, it is believed that the present invention will be better understood from the following description.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied.

The term "oral care composition", as used herein, includes a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice, tooth gel, subgingival gel, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

The term "dentifrice composition", as used herein, includes tooth or subgingival-paste, gel, or liquid formulations unless otherwise specified. The dentifrice composition may be a single-phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

"Active and other ingredients" useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

The term "orally acceptable carrier" comprises one or more compatible solid or liquid excipients or diluents which are suitable for topical oral administration. By "compatible," as used herein, is meant that the components of the composition are capable of being commingled without interaction in a manner which would substantially reduce the composition's stability and/or efficacy. The carriers or excipients of the present invention can include the usual and conventional components of mouthwashes or mouth rinses, as more fully described hereinafter: Mouthwash or mouth rinse carrier materials typically include, but are not limited to one or more of water, alcohol, humectants, surfactants, and acceptance improving agents, such as flavoring, sweetening, coloring and/or cooling agents.

The term "substantially free" as used herein refers to the presence of no more than 0.05%, preferably no more than 0.01%, and more preferably no more than 0.001%, of an indicated material in a composition, by total weight of such composition.

The term "essentially free" as used herein means that the indicated material is not deliberately added to the composition, or preferably not present at analytically detectable levels. It is meant to include compositions whereby the indicated material is present only as an impurity of one of the other materials deliberately added.

While compositions and methods are described herein in terms of "comprising" various components or steps, the compositions and methods can also "consist essentially of" or "consist of" the various components or steps, unless stated otherwise.

As used herein, the word "or" when used as a connector of two or more elements is meant to include the elements individually and in combination; for example, X or Y, means X or Y or both.

As used herein, the articles "a" and "an" are understood to mean one or more of the material that is claimed or described, for example, "an oral care composition" or "a bleaching agent."

All measurements referred to herein are made at about 23° C. (i.e. room temperature) unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, and so forth.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein.

The term "about" means that amounts, sizes, formulations, parameters, and other quantities and characteristics are not and need not be exact, but can be approximate and/or larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

The dentifrice composition can be in any suitable form, such as a solid, liquid, powder, paste, or combinations thereof. The oral care composition can be dentifrice, tooth gel, subgingival gel, mouth rinse, mousse, foam, mouth spray, lozenge, chewable tablet, chewing gum, tooth whitening strips, floss and floss coatings, breath freshening dissolvable strips, or denture care or adhesive product. The components of the dentifrice composition can be incorporated into a film, a strip, a foam, or a fiber-based dentifrice composition. The dentifrice composition can include a variety of active and inactive ingredients, such as, for example, but not limited to a tin ion source, a stabilizing polyol, a gum strengthening polyol, an abrasive, water, a fluoride ion source, zinc ion source, one or more polyphosphates, additional humectants, surfactants, other ingredients, and the like, as well as any combination thereof, as described below.

Tin

The oral care compositions of the present invention comprise tin. The tin can be provided by a tin ion source. The tin ion source can be any suitable compound that can provide tin ions in an oral care composition and/or deliver tin ions to the oral cavity when the dentifrice composition is applied to the oral cavity. The tin ion source can comprise one or more tin containing compounds, such as stannous fluoride, stannous chloride, stannous bromide, stannous iodide, stannous oxide, stannous sulfate, stannous sulfide, stannic fluoride, stannic chloride, stannic bromide, stannic iodide, stannic sulfide, and/or mixtures thereof. Preferably, the tin ion source can comprise stannous fluoride, stannous chloride, and/or mixture thereof.

The oral care compositions can comprise from about 0.0025% to about 5%, from about 0.2% to about 1%, from about 0.5% to about 1.5%, or from about 0.3% to about 0.6%, by weight of the oral care composition, of a tin ion source.

Stabilizing Polyol

The oral care compositions of the present invention comprise one or more stabilizing polyols. A polyol is an organic compound with more than one hydroxyl functional groups. The stabilizing polyol can be any suitable polyol that can weakly associate, interact, or bond to tin ions while the oral care composition is stored prior to use. The stabilizing polyol can be a sugar alcohol, a monosaccharide, a disaccharide, a polysaccharide, or a non-reducing sugar. Sugar alcohols are a class of polyols that can be obtained through the hydrogenation of sugar compounds with the formula $(CHOH)_nH_2$, where n=4-6. Preferably, n is 5 and/or 6 because these compounds have been shown to unexpectedly interact with tin ion sources to create soluble complexes, as described herein, at a reasonable formulation cost. Non-reducing sugars are a class of saccharides that do not generate any compounds containing an aldehyde functional group. Non-reducing sugars are stable in water and do not react with weak oxidizing agents to produce sugar alcohols. Examples of suitable non-reducing sugars include, but are not limited to, sucrose, trehalose, raffinose, stachyose, verbascose, or combinations thereof. Preferably, the stabilizing polyol is a sugar alcohol.

The stabilizing polyol can be xylitol, sorbitol, mannitol, lactitol, galactitol, isomalt, and/or combinations thereof. Preferably, the stabilizing polyol can be a sugar alcohol with the formula $(CHOH)_nH_2$, where n=5 and/or 6. More preferably, the stabilizing polyol can be xylitol, sorbitol, galactitol, and/or mixtures thereof.

The oral care composition can comprise 0.01% to about 70%, from about 5% to about 70%, from about 5% to about 50%, from about 10% to about 60%, or from about 20% to about 80%, by weight of the oral care composition, of a stabilizing polyol.

The oral care composition can also comprise an additional humectant, have low levels of an additional humectant, or be free of an additional humectant. Humectants, in general, serve to add body or "mouth texture" to an oral care composition or dentifrice as well as preventing the oral care composition from drying out. Suitable humectants include polyethylene glycol (at a variety of different molecular weights), propylene glycol, glycerin, erythritol, xylitol, sorbitol, mannitol, butylene glycol, lactitol, hydrogenated starch hydrolysates, and/or mixtures thereof. The oral care composition can comprise a polyol and an additional humectant, such as xylitol to interact with the tin ion source and glycerin to prevent the oral care composition from drying out during storage or add body to the oral care composition. The oral care composition can also be free of an additional humectant because the polyol can serve as both the polyol and the additional humectant, such as when the polyol is xylitol, sorbitol, or combinations thereof.

The oral care composition can comprise one or more humectants each at a level of from about 0.01% to about 70%, from about 5% to about 50%, from about 10% to about 60%, or from about 20% to about 80%, by weight of the oral care composition.

Gum Strengthening Polyol

The oral care compositions of the present invention comprise one or more gum strengthening polyols. While polyols with five or more carbon atoms have been shown to stabilize tin ions, polyols with seven or more hydroxyl functional groups have been shown to additionally strengthen the barrier function of epithelial cells in the oral cavity. While polyols with seven or more hydroxyl functional groups can be cost prohibitive, as described herein, a combination of a polyol with five or six carbon atoms (the "stabilizing polyol") with apolyol with seven or more hydroxyl functional groups (the "gum strengthening polyol") can provide a similar benefit with a reasonable cost.

The gum strengthening polyol can be a sugar alcohol, a monosaccharide, a disaccharide, a polysaccharide, or a non-reducing sugar. Sugar alcohols are a class of polyols that can be obtained through the hydrogenation of sugar compounds with the formula $(CHOH)_nH_2$, where n is seven or more, such as isomalt, maltitol, lactitol, maltotriitol, maltotetraitol, polyglycitol, or combinations thereof. Preferably, n is from about 7 to about 12. Even more preferably, the gum strengthening polyol is isomalt, maltitol, lactitol, or combinations thereof.

Non-reducing sugars are a class of saccharides that do not generate any compounds containing an aldehyde functional group. Non-reducing sugars are stable in water and do not react with weak oxidizing agents to produce sugar alcohols. Non-reducing sugars cannot donate electrons to other molecules, and is typically a di, tri, terta, penta saccharide, such as sucrose, trehalose, raffinose, stachyose, verbascose, or combinations thereof. Preferably, the gum strengthening polyol is trehalose. The gum barrier properties can be obtained from a combination mixture of polyols whereby all have seven or greater hydroxyl functional groups.

The oral care composition can comprise 0.025% to about 20%, from about 0.01% to about 15%, from about 1% to about 10%, from about 0.01% to about 15%, or from about 0.0025% to about 10%, by weight of the oral care composition, of a gum strengthening polyol.

Abrasive

The oral care composition of the present invention can comprise abrasive. Abrasives can be added to oral care formulations to help remove surface stains from teeth. Preferably, the abrasive is a calcium abrasive or a silica abrasive.

The calcium abrasive can be any suitable abrasive compound that can provide calcium ions in an oral care composition and/or deliver calcium ions to the oral cavity when the oral care composition is applied to the oral cavity. The oral care composition can comprise from about 5% to about 70%, from about 10% to about 60%, from about 20% to about 50%, from about 25% to about 40%, or from about 1% to about 50% of a calcium abrasive. The calcium abrasive can comprise one or more calcium abrasive compounds, such as calcium carbonate, precipitated calcium carbonate (PCC), ground calcium carbonate (GCC), chalk, dicalcium phosphate, calcium pyrophosphate, and/or mixtures thereof.

The oral care composition can also comprise a silica abrasive, such as silica gel (by itself, and of any structure), precipitated silica, amorphous precipitated silica (by itself, and of any structure as well), hydrated silica, and/or combinations thereof. The oral care composition can comprise from about 5% to about 70%, from about 10% to about 60%, from about 10% to about 50%, from about 20% to about 50%, from about 25% to about 40%, or from about 1% to about 50% of a silica abrasive.

The oral care composition can also comprise another abrasive, such as bentonite, perlite, titanium dioxide, alumina, hydrated alumina, calcined alumina, aluminum silicate, insoluble sodium metaphosphate, insoluble potassium metaphosphate, insoluble magnesium carbonate, zirconium silicate, particulate thermosetting resins and other suitable abrasive materials. The oral care composition can comprise from about 5% to about 70%, from about 10% to about 60%, from about 10% to about 50%, from about 20% to about 50%, from about 25% to about 40%, or from about 1% to about 50% of another abrasive.

Alternatively, the oral care composition can be substantially free of, essentially free of, or free of silica, alumina, or any other non-calcium abrasive. The oral care composition can comprise less than about 5%, less than about 1%, less than about 0.5%, less than about 0.1%, or 0% of a non-calcium abrasive, such as silica and/or alumina.

Water

The oral care composition of the present invention can be a dentifrice composition that is anhydrous, a low water formulation, or a high water formulation. In total, the oral care composition can comprise from 0% to about 99%, about 20% or greater, about 30% or greater, about 50% or greater, up to about 45%, or up to about 75%, by weight of the composition, of water. Preferably, the water is USP water.

In a high water dentifrice formulation, the dentifrice composition comprises from about 45% to about 75%, by weight of the composition, of water. The high water dentifrice composition can comprise from about 45% to about 65%, from about 45% to about 55%, or from about 46% to about 54%, by weight of the composition, of water. The water may be added to the high water dentifrice formulation and/or may come into the composition from the inclusion of other ingredients.

In a low water dentifrice formulation, the dentifrice composition comprises from about 10% to about 45%, by weight of the composition, of water. The low water dentifrice composition can comprise from about 10% to about 35%, from about 15% to about 25%, or from about 20% to about 25%, by weight of the composition, of water. The water may be added to the low water dentifrice formulation and/or may come into the composition from the inclusion of other ingredients.

In an anhydrous dentifrice formulation, the dentifrice composition comprises less than about 10%, by weight of the composition, of water. The anhydrous dentifrice composition comprises less than about 5%, less than about 1%, or 0%, by weight of the composition, of water. The water may be added to the anhydrous formulation and/or may come into the dentifrice composition from the inclusion of other ingredients.

The dentifrice composition can also comprise other orally acceptable carrier materials, such as alcohol, humectants, polymers, surfactants, and acceptance improving agents, such as flavoring, sweetening, coloring and/or cooling agents.

The oral care composition can also be a mouth rinse formulation. A mouth rinse formulation can comprise from about 75% to about 99%, from about 75% to about 95%, or from about 80% to about 95% of water.

pH

The oral care composition can comprise one or more buffering agents. Buffering agents, as used herein, refer to agents that can be used to adjust the slurry pH of the oral care compositions to a range of greater than 7, from greater than 7 to about 14, about 7.5 or greater, about 8 or greater, from about 7.5 to about 10, greater than 7 to about 10, from about 8 to about 10, from about 8 to about 9.5, or from about 8.5 to about 9. The pH of a mouthrinse solution can be determined as the pH of the neat solution. The pH of a dentifrice composition can be determined as a slurry pH, which is the pH of a mixture of the dentifrice composition and water, such as a 1:4, 1:3, or 1:2 mixture of the dentifrice composition and water. The buffering agents include alkali metal hydroxides, carbonates, sesquicarbonates, borates, silicates, phosphates, imidazole, and mixtures thereof. Specific buffering agents include monosodium phosphate, trisodium phosphate, sodium hydroxide, potassium hydroxide, alkali metal carbonate salts, sodium carbonate, imidazole, pyrophosphate salts, citric acid, and sodium citrate. The oral care composition can comprise one or more buffering agents each at a level of from about 0.1% to about 30%, from about 1% to about 10%, or from about 1.5% to about 3%, by weight of the present composition.

Zinc

The oral care composition can comprise zinc. The zinc can be provided by a zinc ion source. The zinc ion source can comprise one or more zinc containing compounds, such as zinc fluoride, zinc lactate, zinc oxide, zinc phosphate, zinc chloride, zinc acetate, zinc hexafluorozirconate, zinc sulfate, zinc tartrate, zinc gluconate, zinc citrate, zinc malate, zinc glycinate, zinc pyrophosphate, zinc metaphosphate, zinc oxalate, and/or zinc carbonate.

The zinc ion source may be present in the total oral care composition at an amount of from about 0.01% to about 5%, from about 0.2% to about 1%, from about 0.5% to about 1.5%, or from about 0.3% to about 0.6%, by weight of the oral care composition.

Fluoride

The oral care composition can comprise fluoride. The fluoride can be provided by a fluoride ion source. The fluoride ion source can comprise one or more fluoride containing compounds, such as stannous fluoride, sodium fluoride, potassium fluoride, amine fluoride, sodium monofluorophosphate, zinc fluoride, and/or mixtures thereof.

The fluoride ion source and the tin ion source can be the same compound, such as for example, stannous fluoride, which can generate tin ions and fluoride ions. Additionally, the fluoride ion source and the tin ion source can be separate compounds, such as when the tin ion source is stannous chloride and the fluoride ion source is sodium monofluorophosphate or sodium fluoride.

The fluoride ion source and the zinc ion source can be the same compound, such as for example, zinc fluoride, which can generate zinc ions and fluoride ions. Additionally, the fluoride ion source and the zinc ion source can be separate compounds, such as when the zinc ion source is zinc phosphate and the fluoride ion source is stannous fluoride.

The oral care composition can comprise a fluoride ion source capable of providing from about 50 ppm to about 3500 ppm, and preferably from about 500 ppm to about 3000 ppm of free fluoride ions. To deliver the desired amount of fluoride ions, the fluoride ion source may be present in the total oral care composition at an amount of from about 0.0025% to about 5%, from about 0.2% to about 1%, from about 0.5% to about 1.5%, or from about 0.3% to about 0.6%, by weight of the oral care composition.

Polyphosphates

The oral care composition can comprise polyphosphate. The polyphosphate can be provided by a polyphosphate source. A polyphosphate source can comprise one or more polyphosphate molecules. Polyphosphates are a class of materials obtained by the dehydration and condensation of orthophosphate to yield linear and cyclic polyphosphates of varying chain lengths. Thus, polyphosphate molecules are generally identified with an average number (n) of polyphosphate molecules, as described below. A polyphosphate is generally understood to consist of two or more phosphate molecules arranged primarily in a linear configuration, although some cyclic derivatives may be present.

Preferred polyphosphates are those having an average of two or more phosphate groups so that surface adsorption at effective concentrations produces sufficient non-bound phosphate functions, which enhance the anionic surface charge as well as hydrophilic character of the surfaces. Preferred in this invention are the linear polyphosphates having the formula: $XO(XPO_3)_nX$, wherein X is sodium, potassium, ammonium, or any other alkali metal cations and n averages from about 2 to about 21. Alkali earth metal cations, such as calcium, are not preferred because they tend to form insoluble fluoride salts from aqueous solutions comprising a fluoride ions and alkali earth metal cations. Thus, the oral care compositions disclosed herein can be free of or substantially free of calcium pyrophosphate.

Some examples of suitable polyphosphate molecules include, for example, pyrophosphate (n=2), tripolyphosphate (n=3), tetrapolyphosphate (n=4), sodaphos polyphosphate (n=6), hexaphos polyphosphate (n=13), benephos polyphosphate (n=14), hexametaphosphate (n=21), which is also known as Glass H. Polyphosphates can include those polyphosphate compounds manufactured by FMC Corporation, ICL Performance Products, and/or Astaris.

The oral care composition can comprise from about 0.01% to about 15%, from about 0.1% to about 10%, from about 0.5% to about 5%, from about 1 to about 20%, or about 10% or less, by weight of the oral care composition, of the polyphosphate source.

Surfactants

The oral care composition can comprise one or more surfactants. The surfactants can be used to make the compositions more cosmetically acceptable. The surfactant is preferably a detersive material which imparts to the composition detersive and foaming properties. Suitable surfactants are safe and effective amounts of anionic, cationic, nonionic, zwitterionic, amphoteric and betaine surfactants, such as sodium lauryl sulfate, sodium lauryl isethionate, sodium lauroyl methyl isethionate, sodium cocoyl glutamate, sodium dodecyl benzene sulfonate, alkali metal or ammonium salts of lauroyl sarcosinate, myristoyl sarcosinate, palmitoyl sarcosinate, stearoyl sarcosinate and oleoyl sarcosinate, polyoxyethylene sorbitan monostearate, isostearate and laurate, sodium lauryl sulfoacetate, N-lauroyl sarcosine, the sodium, potassium, and ethanolamine salts of N-lauroyl, N-myristoyl, or N-palmitoyl sarcosine, polyethylene oxide condensates of alkyl phenols, cocoamidopropyl betaine, lauramidopropyl betaine, palmityl betaine, sodium cocoyl glutamate, and the like. Sodium lauryl sulfate is a preferred surfactant. The oral care composition can comprise one or more surfactants each at a level from about 0.01% to about 15%, from about 0.3% to about 10%, or from about 0.3% to about 2.5%, by weight of the oral care composition.

Thickening Agents

The oral care composition can comprise one or more thickening agents. Thickening agents can be useful in the oral care compositions to provide a gelatinous structure that stabilizes the toothpaste against phase separation. Suitable thickening agents include polysaccharides, polymers, and/or silica thickeners. Some non-limiting examples of polysaccharides include starch; glycerite of starch; gums such as gum karaya (sterculia gum), gum tragacanth, gum arabic, gum ghatti, gum acacia, xanthan gum, guar gum and cellulose gum; magnesium aluminum silicate (Veegum); carrageenan; sodium alginate; agar-agar; pectin; gelatin; cellulose compounds such as cellulose, carboxymethyl cellulose, hydroxyethyl cellulose, hydroxypropyl cellulose, hydroxymethyl cellulose, hydroxymethyl carboxypropyl cellulose, methyl cellulose, ethyl cellulose, and sulfated cellulose; natural and synthetic clays such as hectorite clays; and mixtures thereof.

The thickening agent can comprise polysaccharides. Polysaccharides that are suitable for use herein include carageenans, gellan gum, locust bean gum, xanthan gum, carbomers, poloxamers, modified cellulose, and mixtures thereof. Carageenan is a polysaccharide derived from seaweed. There are several types of carageenan that may be distinguished by their seaweed source and/or by their degree of and position of sulfation. The thickening agent can comprise kappa carageenans, modified kappa carageenans, iota carageenans, modified iota carageenans, lambda carrageenan, and mixtures thereof. Carageenans suitable for use herein include those commercially available from the FMC Company under the series designation "Viscarin," including but not limited to Viscarin TP 329, Viscarin TP 388, and Viscarin TP 389.

The thickening agent can comprise one or more polymers. The polymer can be a polyethylene glycol (PEG), a polyvinylpyrrolidone (PVP), a polyacrylic acid polymer, a polymer derived from at least one acrylic acid monomer, a copolymer of maleic anhydride and methyl vinyl ether, a crosslinked polyacrylic acid polymer, of various weight percentages of the oral care composition as well as various ranges of average molecular ranges.

The thickening agent can comprise inorganic thickening agents. Some non-limiting examples of suitable inorganic thickening agents include colloidal magnesium aluminum silicate, silica thickeners. Useful silica thickeners include, for example, include, as a non-limiting example, an amorphous precipitated silica such as ZEODENT® 165 silica. Other non-limiting silica thickeners include ZEODENT® 153, 163, and 167, and ZEOFREE® 177 and 265 silica products, all available from Evonik Corporation, and AEROSIL® fumed silicas.

Preferably, the thicking agent can comprise at least one of a linear sulfated polysaccharide, a natural gum, a cellulose derivative, a polyacrylic acid polymer, or combinations thereof.

The oral care composition can comprise from 0.01% to about 15%, from 0.1% to about 10%, from about 0.2% to about 5%, or from about 0.5% to about 2% of one or more thickening agents.

Chelant

The oral care composition can comprise one or more chelants, having a molecular weight (MW) of less than 1000. The term "chelant", as used herein means a bi- or multidentate ligand having at least two groups capable of binding to the divalent metal ions. Typically, those chelants useful herein will also form water soluble complexes with the stannous ions. Oral care compositions comprising silica abrasives typically include one or more chelants to reversibly bind the tin ions to prevent the tin ions from irreversibly binding to the surface of silica particles. Suitable chelants herein include $C_2$-$C_6$ dicarboxylic and tricarboxylic acids, such as succinic acid, malic acid, tartaric acid and citric acid; $C_3$-$C_6$ monocarboxylic acids substituted with hydroxyl, such as gluconic acid; picolinic acid; amino acids such as glycine; phytic acid, salts thereof and mixtures thereof. Preferably, the chelant is sodium gluconate or a salt of citric acid.

The oral care composition can comprise one or more chelants each at a level of from about 0.01% to about 5%, from about 0.2% to about 2%, from about 0.5% to about 1.5%, or from about 1% to about 3%, by weight of the oral care composition. Alternatively, the oral care composition can be substantially free of, essentially free of, or free of a chelant because the oral care compositions of the present invention comprises a calcium abrasive instead of a silica abrasive. Additionally, the oral care composition can comprise one or more chelants each at a level of less than about 1%, less than about 0.5%, less than about 0.1%, or less than about 0.01%, by weight of the oral care composition.

Other Ingredients

The oral care composition can comprise a variety of other ingredients, such as flavoring agents, sweeteners, colorants, preservatives, buffering agents, or other ingredients suitable for use in oral care compositions, as described below.

Flavoring agents also can be added to the oral care composition. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the paramenthan carboxyamide agents such as N-ethyl-p-menthan-3-carboxamide (known commercially as "WS-3") or N-(Ethoxycarbonylmethyl)-3-p-menthanecarboxamide (known commercially as "WS-5"), and mixtures thereof. A flavor system is generally used in the compositions at levels of from about 0.001% to about 5%, by weight of the oral care composition. These flavoring agents generally comprise mixtures of aldehydes, ketones, esters, phenols, acids, and aliphatic, aromatic and other alcohols.

Sweeteners can be added to the oral care composition to impart a pleasing taste to the product. Suitable sweeteners include saccharin (as sodium, potassium or calcium saccharin), cyclamate (as a sodium, potassium or calcium salt), acesulfame-K, thaumatin, neohesperidin dihydrochalcone, ammoniated glycyrrhizin, dextrose, levulose, sucrose, mannose, sucralose, *stevia*, and glucose.

Colorants can be added to improve the aesthetic appearance of the product. Suitable colorants include without limitation those colorants approved by appropriate regulatory bodies such as the FDA and those listed in the European Food and Pharmaceutical Directives and include pigments, such as $TiO_2$, and colors such as FD&C and D&C dyes.

Preservatives also can be added to the oral care compositions to prevent bacterial growth. Suitable preservatives approved for use in oral compositions such as methylparaben, propylparaben, benzoic acid, and sodium benzoate can be added in safe and effective amounts.

Titanium dioxide may also be added to the present composition. Titanium dioxide is a white powder which adds opacity to the compositions. Titanium dioxide generally comprises from about 0.25% to about 5%, by weight of the oral care composition.

Other ingredients can be used in the oral care composition, such as desensitizing agents, healing agents, other caries preventative agents, chelating/sequestering agents, vitamins, amino acids, proteins, other anti-plaque/anti-calculus agents, opacifiers, antibiotics, anti-enzymes, enzymes, pH control agents, oxidizing agents, antioxidants, and the like.

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

Experimental Methods
Solubility of Tin Ions at a pH of Greater than 7

A 30% (w/w) solution was prepared for each polyol or combination of polyols was prepared using the appropriate amount of the pure polyol and deionized water. Next, 46 g of the 30% (w/w) polyol solution was placed in a 250 mL glass beaker with a stirring bar on top of a magnetic stirring apparatus. 21 g of deionized water was added to the glass beaker and the magnetic stirring apparatus was started to commence stirring of the solution. A pH electrode was connected to a pH meter (VWR Scientific, Model 9100, Radnor, PA) and the pH electrode (ThermoFisher Scientific, Orion 8165BNWP, Waltham, MA) was placed in the stirring polyol solution.

0.45 grams of a tin ion source, such as stannous fluoride, was added to the stirring polyol solution. The pH was recorded once the tin ion source was completely added. The pH of the solution was increased by dropwise addition of a 33% (w/w) solution of NaOH.

Solubility of Tin Ions at a pH of Less than 7

A 30% (w/w) solution was prepared for each polyol or combination of polyols was prepared using the appropriate amount of the pure polyol and deionized water. Next, 46 g of the 30% (w/w) polyol solution was placed in a 250 mL glass beaker with a stirring bar on top of a magnetic stirring apparatus. 21 g of deionized water was added to the glass beaker and the magnetic stirring apparatus was started to commence stirring of the solution. A pH electrode was connected to a pH meter (VWR Scientific, Model 9100, Radnor, PA) and the pH electrode (ThermoFisher Scientific, Orion 8165BNWP, Waltham, MA) was placed in the stirring polyol solution.

0.45 grams of a tin ion source, such as stannous fluoride, was added to the stirring polyol solution. The pH was recorded once the tin ion source was completely added. The pH of the solution was decreased by dropwise addition of a 33% (w/w) solution of HCl.

TABLE 1

Polyol Solutions with $SnF_2$

| Polyol | pH 2-4 | pH 4-6 | pH 6-8 | pH 8-10 |
|---|---|---|---|---|
| Sorbitol | clear | cloudy | cloudy | clear |
| Trehalose (8 OH) | clear | cloudy | cloudy | cloudy |
| Isomalt (10 OH) | clear | cloudy | cloudy | cloudy |
| Sorbitol (6 OH):Trehalose (8 OH) (1:1) | clear | cloudy | cloudy | clear |
| Sorbitol (6 OH):Trehalose (8 OH) (1:3) | clear | cloudy | cloudy | clear |
| Sorbitol (6 OH):Isomalt (10 OH) (1:1) | clear | cloudy | cloudy | clear |

Figure 2:
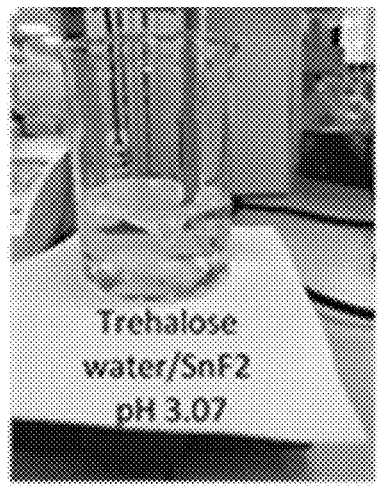
FIG. 2 is an illustration of the solubilization of tin ions at various pH conditions with trehalose.
Figure 2:
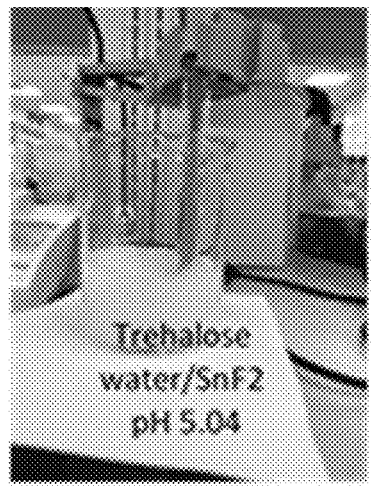
Figure 2:
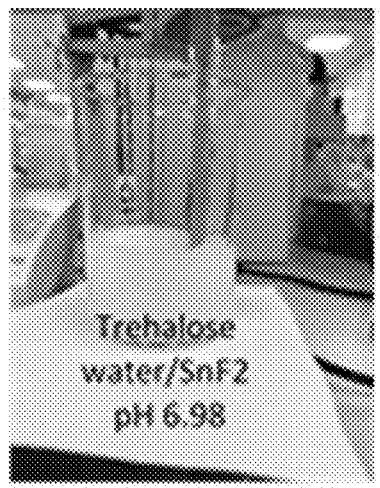
Figure 2:
Figure 3:
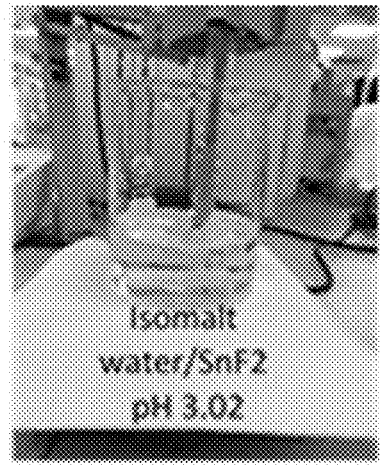
FIG. 3 is an illustration of the solubilization of tin ions at various pH conditions with isomalt.
Figure 3:
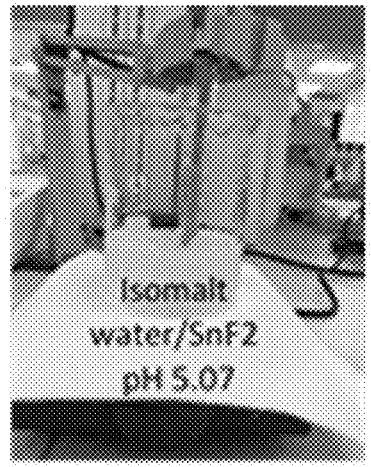
Figure 3:
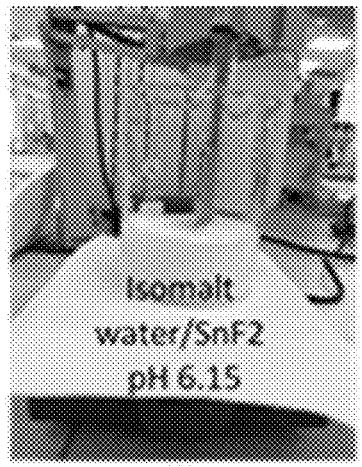
Figure 3:
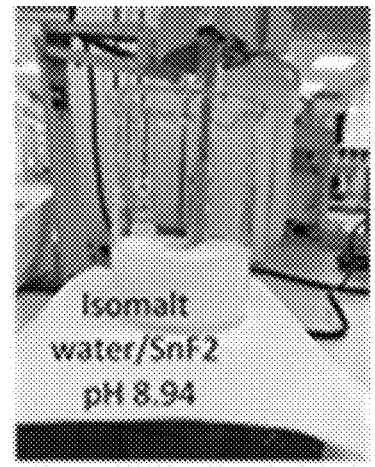
Figure 4:
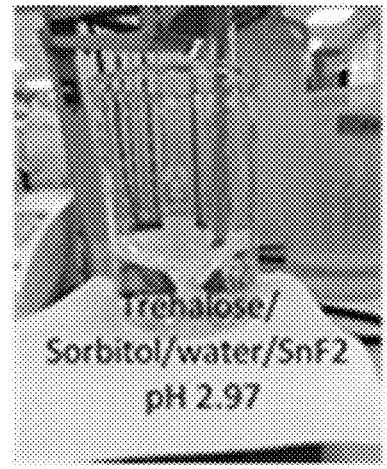
FIG. 4 is an illustration of the solubilization of tin ions at various pH conditions with trehalose and sorbitol at a 1:1 ratio.
Figure 4:
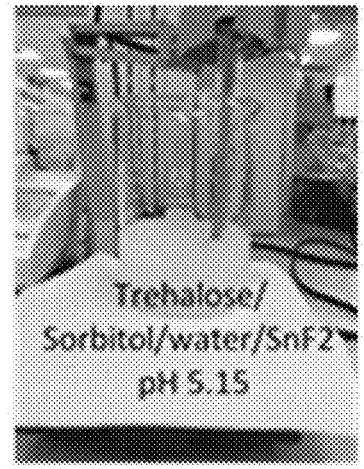
Figure 4:
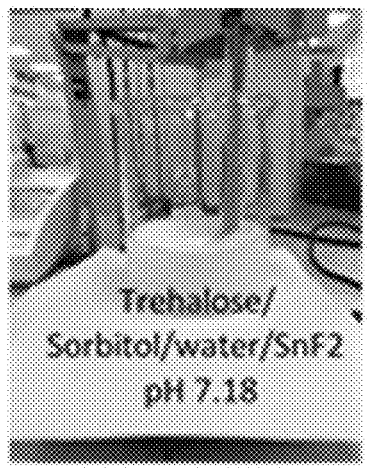
Figure 4:
Figure 5:
FIG. 5 is an illustration of the solubilization of tin ions at various pH conditions with trehalose and sorbitol at a 3:1 ratio.
Figure 5:
Figure 5:
Figure 5:
Figure 6:
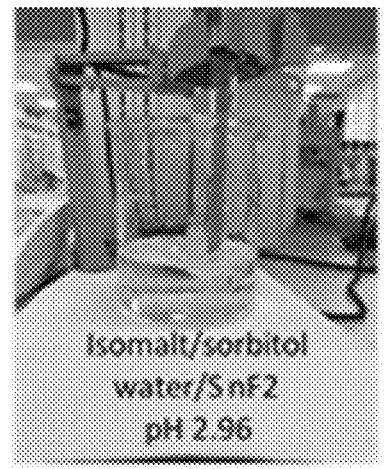
FIG. 6 is an illustration of the solubilization of tin ions at various pH conditions with isomalt and sorbitol at a 1:1 ratio.
Figure 6:
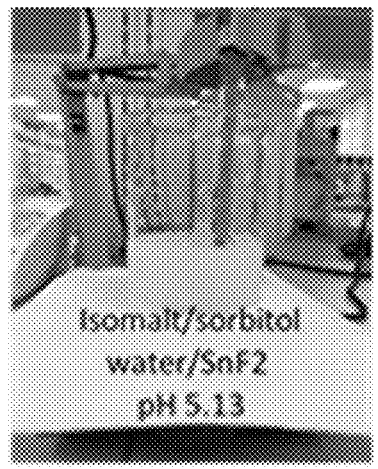
Figure 6:
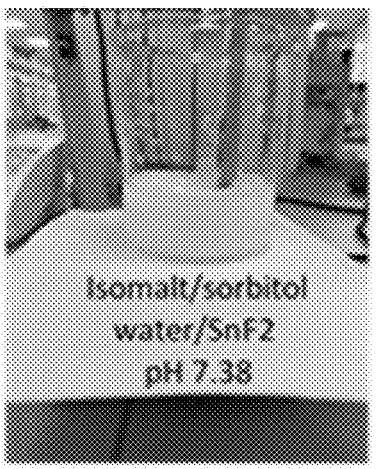
Figure 6:
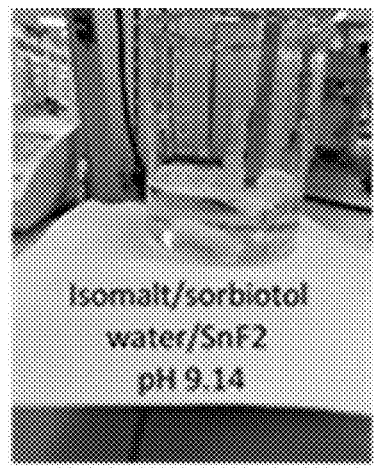

TABLE 1 shows the formation of insoluble tin compounds, such as $Sn(OH)_2$, in the presence of a variety of polyols or combinations of polyols at different pH ranges. A solution that appeared cloudy indicated the formation of insoluble tin complexes. At a pH of greater than 7, a cloudy solution indicated the formation of $Sn(OH)_2$. FIG. 1-6 illustrate TABLE 1 by showing the appearance of each solution described in TABLE 1.

Polyols were screened for their effectiveness at preventing the formation of $Sn(OH)_2$. For example, an aqueous solution of sorbitol and stannous fluoride, was clear at a pH of from 2 to 4. However, as the pH rose, the solution of sorbitol and stannous fluoride appeared cloudy until a pH of from 8 to 10, which appeared clear.

An aqueous solution of trehalose and stannous fluoride, was clear at a pH of from 2 to 4. However, as the pH rose, the solution of trehalose or isomalt and stannous fluoride appeared cloudy at every point above pH of 4.

A 1:1 or 1:3 mixture of sorbitol and trehalose with stannous fluoride, was clear at a pH of from 2 to 4 and from 8 to 10. Additionally, a 1:1 solution of sorbitol and isomalt with stannous fluoride, was clear at a pH of from 2 to 4 and from 8 to 10. Thus, the stabilizing polyol can help to solubilize the stannous fluoride.

While aqueous solutions of less than 4 were also observed as being clear, these pH ranges are undesirable because the solubility of inorganic calcium phosphate compounds, such as hydroxyapatite, is increased at lower pH conditions. In other words, while stannous can be stable at a pH of 4, tooth enamel can also be solubilized under these conditions.

Importantly, TABLE 1 surprisingly demonstrates that tin ions can form soluble complexes with polyols, which prevented the formation of insoluble tin compounds, such as $Sn(OH)_2$ at a high pH. The formation of insoluble tin compounds can decrease the tin ion availability, which can decrease the effectiveness of the tin ion source. While not wishing to be bound by theory, it is believed that sugar alcohols with five or more carbon atoms, such as xylitol (5 carbon atoms) and/or sorbitol (6 carbon atoms), can form complexes with tin ions, such as stannous, which can be soluble in water-based dentifrice compositions at a pH of greater than 7.

Cell Culture

Human gingival epithelial (HGE) cell was maintained in a 37° C. incubator with 5% $CO_2$ saturation. Dulbecco's modified Eagle's medium (DMEM, Gibco) containing 10% fetal calf serum, 1% penicillin-streptomycin was used as the complete culture medium, which was changed every 2-3 days.

Barrier Protection Analysis by Real Time Cell Analyzer (RTCA)

The real time cell analyzer (RTCA) xCELLigence RTCA DP (ACEA Bioscience Inc., San Diego, CA) equipment, based on impedance measurement, was used to monitor the barrier protection of polyols. 50 µl complete culture medium was added to E-plates to obtain background readings, followed by the addition of 100 µl of the cell suspension. The E-plates containing 28000 cell/well were incubated at 37° C., 5% $CO_2$ for 22-24 h until cells were confluent. The culture medium was changed to DMEM or DMEM with 1% of polyols, non reducing sugars or combinations and incubated at 37° C., 5% $CO_2$ for 2 h. The barrier disruptor (capsaicin to a final concentration of 75 µM in this case) was added to wells of E-plate. Impedance as reflected by the Cell Index (CI) was recorded continuously for 16-24 h.

The CI curve was normalized at the time point just before adding polyols. The normalized CI at 3 h after adding of barrier disruptor was compared to blank control to generate the percentage of barrier function % comprimisation.

TABLE 2

Barrier Function

| Treatment | Barrier Function |
|---|---|
| Blank | 100% |
| Barrier Disruptor Capsaicin (75 μM) | 28% |
| Sorbitol | 46% |
| Glycerin | 44% |
| Trehalose | 102% |
| Isomalt | 85% |
| Trehalose:Sorbitol 1:1 | 81% |
| Trehalose:Sorbitol 3:1 | 89% |

TABLE 2 shows the gum barrier protection benefit provided by one or more polyols in response to a barrier disruptor. Treatment with the barrier disruptor (a 75 μM solution of capsaicin) resulted in a barrier function value of 28%. The sugar alcohols sorbitol and glycerin provided a moderate barrier function benefit of 46% and 44%, respectively. Trehalose provided a 102% barrier function benefit. Isomalt provided a 85% barrier function benefit. However, neither trehalose nor isomalt was capable of stabilizing stannous fluoride as shown in TABLE 1 and FIG. 1-6.

Importantly, a mixture of trehalose and sorbitol provided an improved barrier function (81% at 1:1 or 89% at 3:1). Additionally, the mixture of trehalose and sorbitol was capable at stabilizing stannous fluoride at a pH of from 8 to 10. Thus, a mixture of a stabilizing polyol and a gum strengthening polyol stabilizes tin ions at a pH of from 8 to 10 and provides a gum barrier protection benefit.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A dentifrice composition comprising:
   (a) stannous chloride;
   (b) stabilizing polyol, the stabilizing polyol comprising five or six carbon atoms;
   (c) gum strengthening polyol, the gum strengthening polyol comprising seven or more hydroxyl functional groups, and
   (d) from about 10% to about 75%, by weight of the composition, of water,
   wherein the composition has a pH of greater than 7.

2. The composition of claim 1, wherein the composition comprises abrasive.

3. The composition of claim 2, wherein the abrasives comprises silica abrasive, calcium abrasive, or combinations thereof.

4. The composition of claim 3, wherein the composition is essentially free of silica abrasive.

5. The composition of claim 3, wherein the calcium abrasive comprises calcium carbonate, calcium pyrophosphate, or combinations thereof.

6. The composition of claim 1, wherein the pH is from about 8 to about 10.

7. The composition of claim 1, wherein the pH is from about 8 to about 9.5.

8. The composition of claim 1, wherein the stabilizing polyol comprises xylitol, sorbitol, or combinations thereof.

9. The composition of claim 1, wherein the gum strengthening polyol comprises trehalose, rafiose, stachyose, verbascose, isomalt, maltitol, lactitol, maltotriitol, maltotetraitol, polyglycitol, or combinations thereof.

10. The composition of claim 1, wherein the composition comprises zinc.

11. The composition of claim 1, wherein the composition comprises from about 0.01% to about 15%, by weight of the composition, surfactant.

12. The composition of claim 1, wherein the composition comprises thickening agent.

13. The composition of claim 12, wherein the thickening agent comprises a linear sulfated polysaccharide, a natural gum, a cellulose derivative, a polyacrylic acid polymer, or combinations thereof.

14. The composition of claim 1, wherein the composition comprises fluoride.

15. The composition of claim 14, wherein the fluoride comprises sodium fluoride, stannous fluoride, sodium monofluorophosphate, amine fluoride, zinc fluoride, or combinations thereof.

16. The composition of claim 1, wherein the composition is free of fluoride.

17. The composition of claim 1, wherein the composition comprises polyphosphate.

18. The dentifrice composition of claim 17, wherein the polyphosphate comprises pyrophosphate, tripolyphosphate, tetrapolyphosphate, a polyphosphate having 6 phosphate groups, a polyphosphate having 13 phosphate groups, a polyphosphate having 14 phosphate groups, hexametaphosphate, or combinations thereof.

19. The dentifrice composition of claim 1, wherein the composition is free of polyphosphate.

20. The dentifrice composition of claim 1, wherein the composition comprises from about 10% to about 45%, by weight of the composition, of water.

* * * * *